United States Patent [19]

Suzuki

[11] Patent Number: 4,463,755
[45] Date of Patent: Aug. 7, 1984

[54] BREATHING CIRCUIT
[75] Inventor: Tatsuo Suzuki, Yokohama, Japan
[73] Assignee: Terumo Corporation, Tokyo, Japan
[21] Appl. No.: 377,602
[22] Filed: May 13, 1982
[30] Foreign Application Priority Data May 18, 1981 [JP] Japan ................................. 56-74759
May 20, 1981 [JP] Japan ................................. 56-74992
May 20, 1981 [JP] Japan ................................. 56-76310
Dec. 9, 1981 [JP] Japan ............................... 56-197874

[51] Int. Cl.³ ............................................. A61M 16/00
[52] U.S. Cl. ........................... 128/204.18; 128/200.18;
128/200.21; 128/911; 128/205.24
[58] Field of Search ........... 28/204.18, 200.21, 203.28,
28/200.24, 911, 205.24; 138/121, 173

[56] References Cited
U.S. PATENT DOCUMENTS 2,999,497 9/1961 Hamilton et al. .................... 138/121
3,234,969 2/1966 DuMont .............................. 138/121
3,313,319 4/1967 Osborn et al. ....................... 138/121
3,578,777 5/1971 DeGain ................................ 138/173
3,715,454 2/1973 Kleykamp ........................... 138/121
3,874,379 4/1975 Enfield et al. .................. 128/200.21
3,945,378 3/1976 Paluch ............................ 128/203.28
4,007,737 2/1977 Paluch ................................. 128/911
4,265,235 5/1981 Fukunaga ............................ 128/911
4,281,652 8/1981 Miller ................................. 128/911
4,320,754 3/1982 Watson et al. ....................... 128/911

Primary Examiner—Henry J. Recla
Attorney, Agent, or Firm—Frishauf, Holtz, Goodman and Woodward

[57] ABSTRACT

A breathing circuit which comprises a coaxial tube type main tube comprising an inner flexible tube constituting an inhalant circuit and a corrugated outer tube having a larger average wall thickness than said inner tube, encircling the periphery of said inner tube, and defining an exhalant circuit in conjunction with said inner tube; and an inner tube retaining member disposed at least at one end of said coaxial tube type main tube and serving to keep said inner tube and said outer tube at a prescribed distance from each other.

26 Claims, 27 Drawing Figures

U.S. Patent   Aug. 7, 1984   Sheet 1 of 6   4,463,755
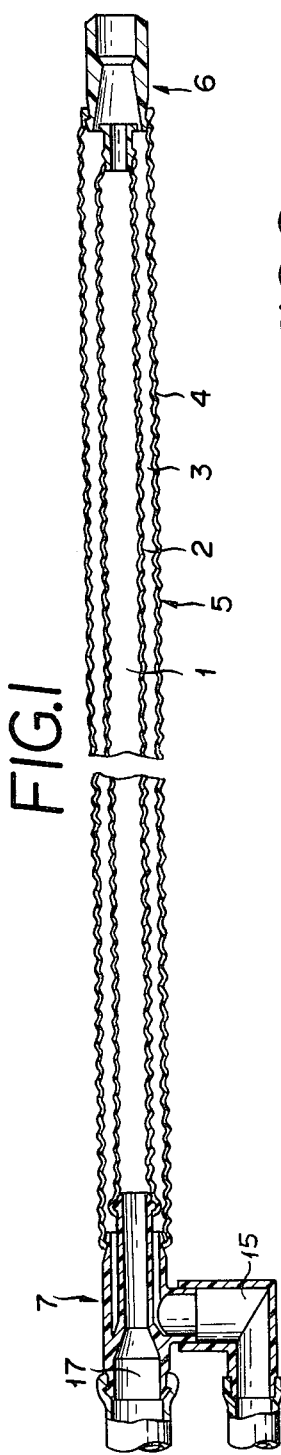
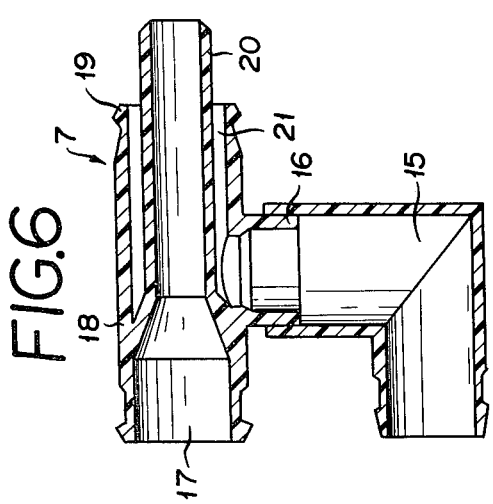
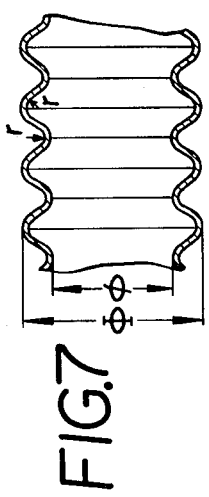
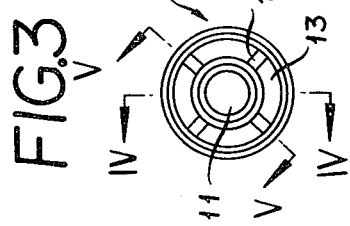
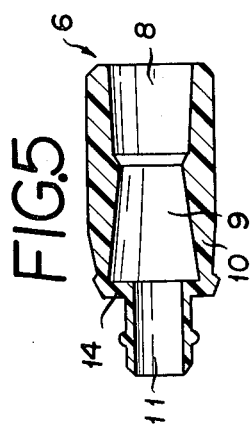
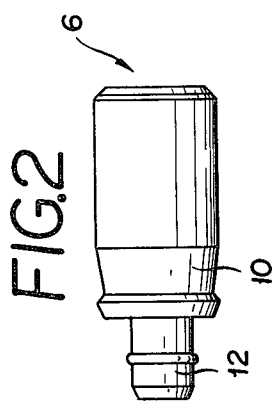
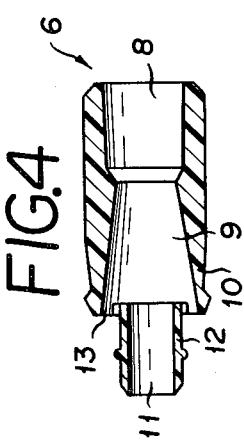

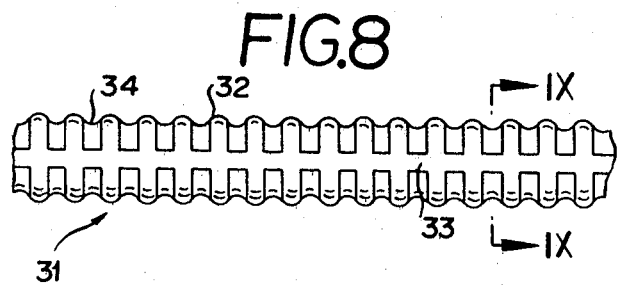
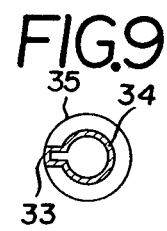
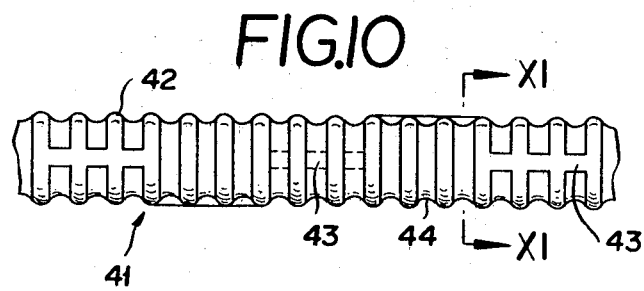
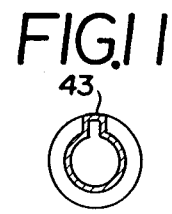
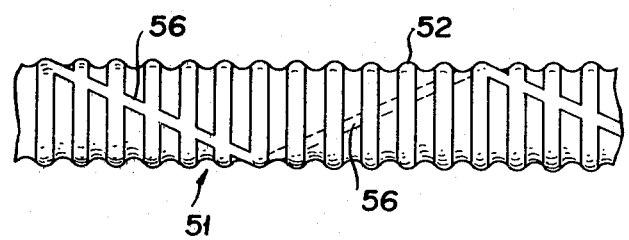
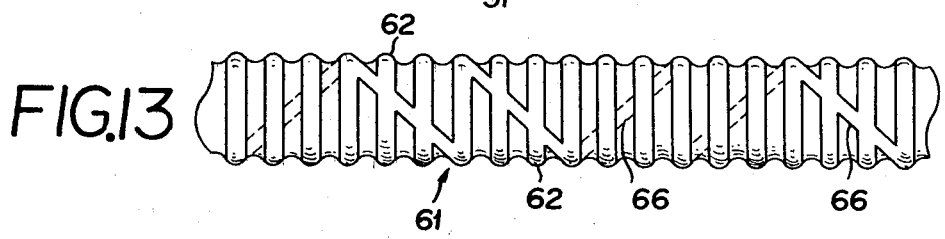
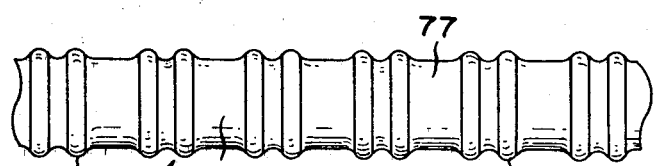
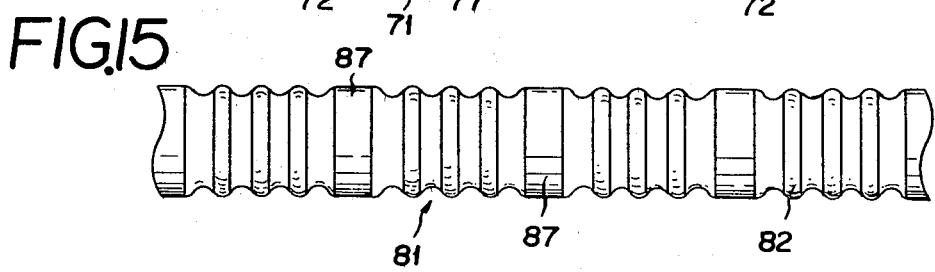

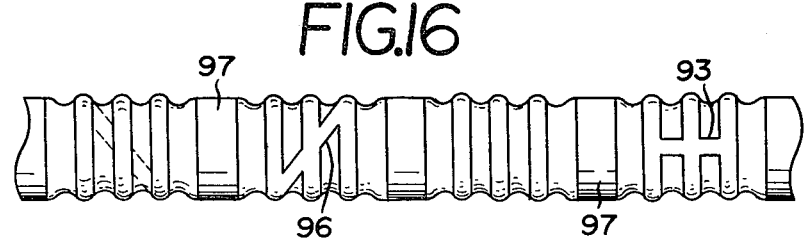
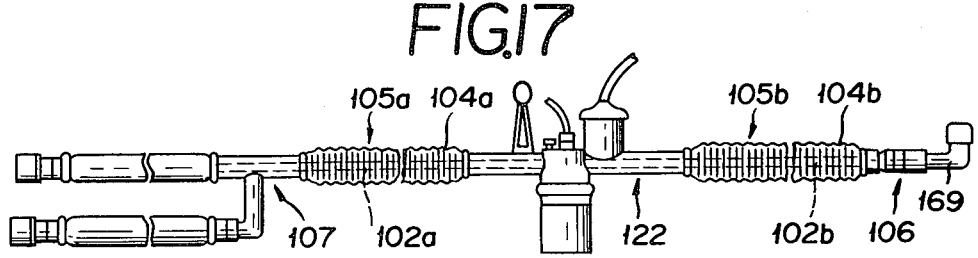
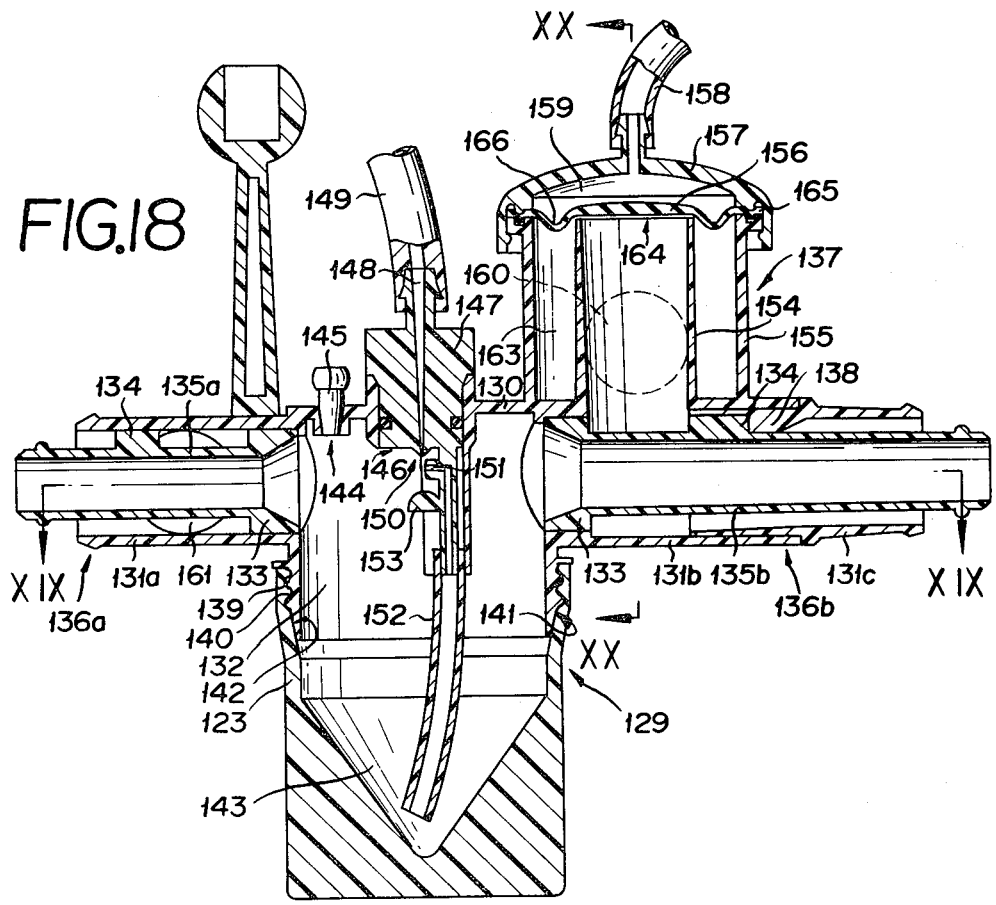

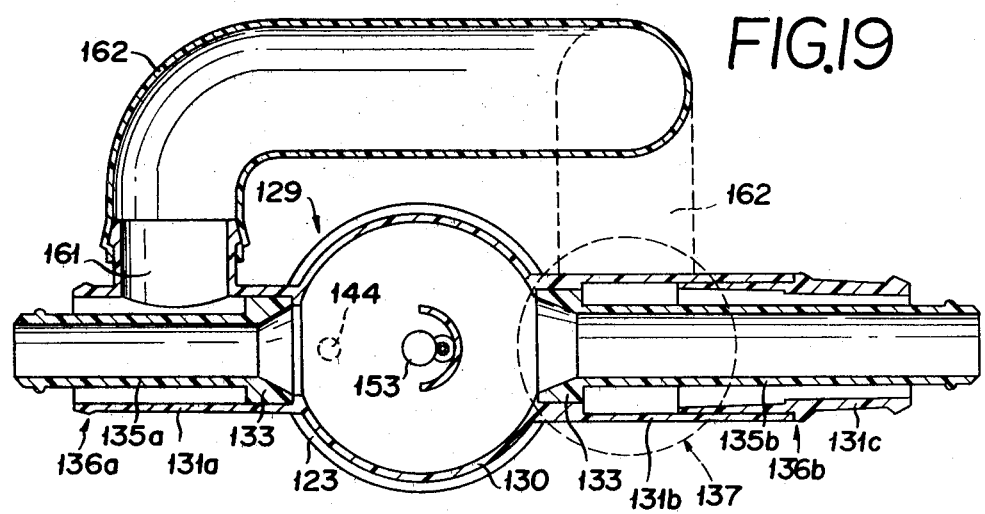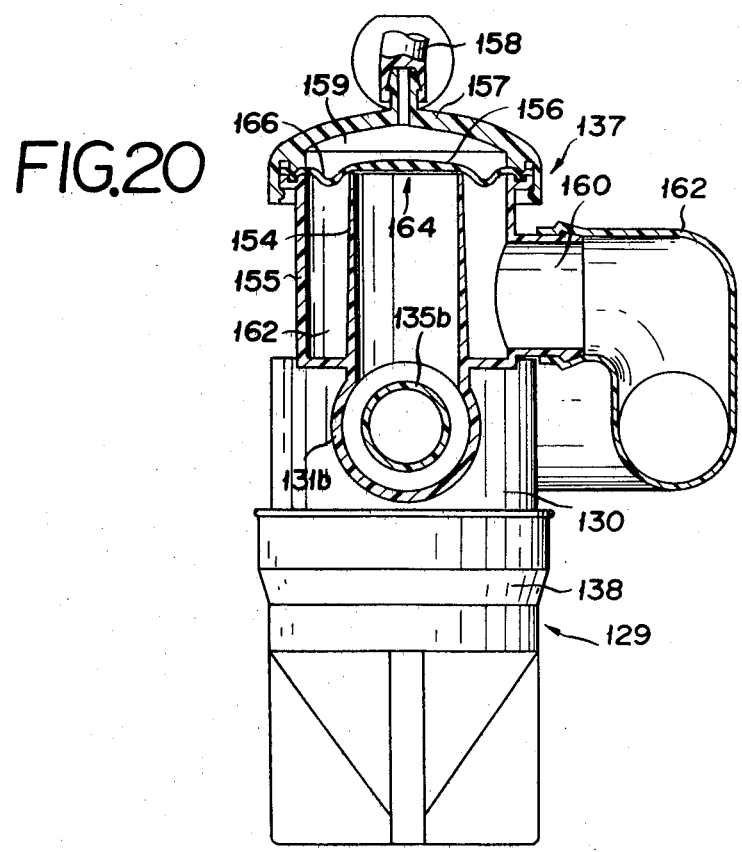

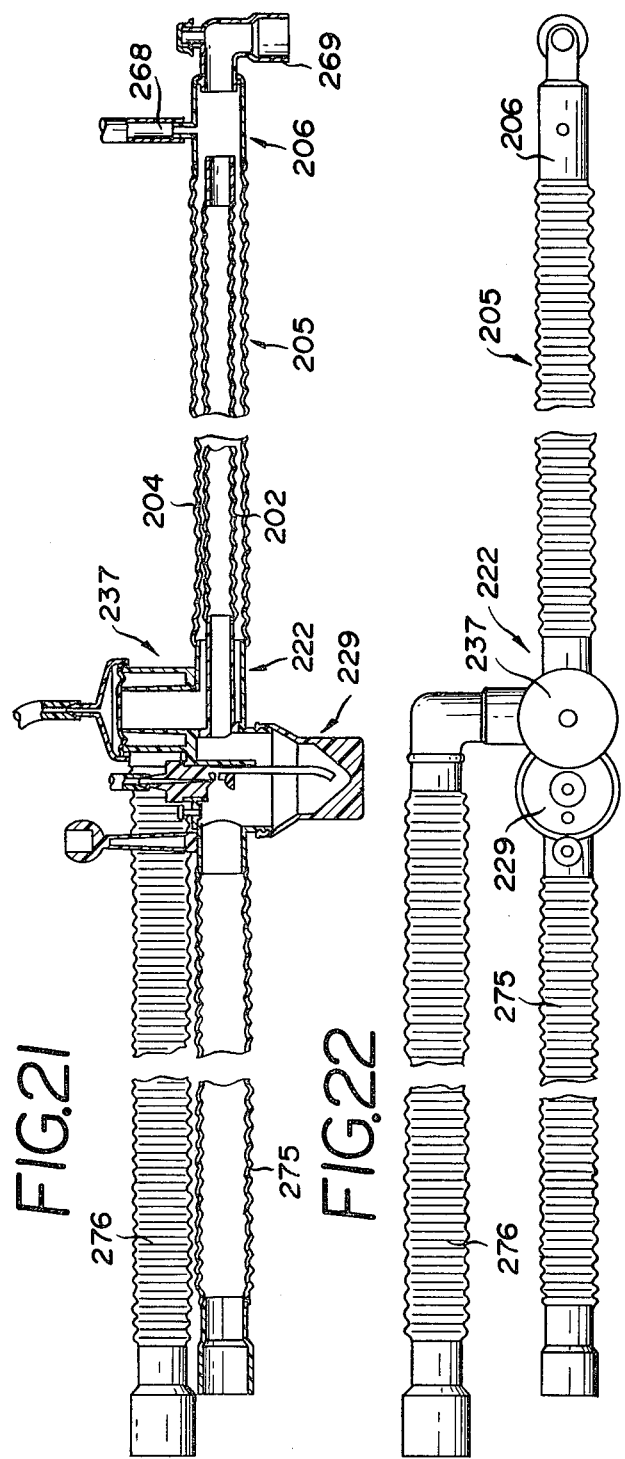

BREATHING CIRCUIT

BACKGROUND OF THE INVENTION

1. Field of the Invention

This invention relates to a breathing circuit. More particularly, the invention relates to a coaxial tube type breathing circuit in an artificial respiratory therapy device.

2. Description of the Prior Art

Various types of breathing circuits are currently in extensive use. They include circuits connected to respirators (otherwise called ventilators) and used for respiratory care, anesthetic circuits used for administering an anesthesizing gas and oxygen gas, for example, to patients, and circuits used for administering medicines, oxygen, and the like for the purpose of inhalant therapy.

These breathing circuits share a basic construction which comprises an inhalant circuit for connecting a respirator, an anesthetizer, or the like to a tracheal catheter, an oral mask, etc. fixated on patients and an exhalant circuit.

In mechanical inhalation and exhalation through the medium of a breathing circuit or anesthetic respiratory circuit, it is generally held that, in due consideration of the water balance and the heat balance of a patient's body, the inhalant breath is desired to have a fairly high temperature as compared with the ambient air, i.e., a temperature not lower than 31° C., though not higher than the temperature of the patient's lungs (38° C. at maximum). Particularly when artificial respiration is continued for a long period, the inhalant breath is required to have a temperature in the range of 32° to 35° C. and a relative humidity of 100%. To give to the inhalant breath such temperature and humidity, a combination heater and humidifier is provided immediately in front of the breathing circuit.

One of the conventional breathing circuits, for example, has a construction wherein an inhalant tube is connected via a combination heater and humidifier to the outlet side of a respirator and an exhalant tube is connected to the inlet side thereof, the two tubes are connected to branched pipes of a Y-shaped connector, and this connector is extended to a tracheal catheter fixated in a patient mouth. Further, a nebulizer adapter to deliver such a medicine as bronchodilator or sputum dissolver in the form of aerosol into the air pipe is inserted halfway along the length of the inhalant tube and an exhalation valve is likewise inserted in the exhalant tube.

Since the breathing circuit of this construction has the inhalant tube and the exhalant tube formed separately of each other, it inevitably has a large overall size and is inconvenient to handle. Further in this breathing circuit, the inhalant gas which is warmed in advance in the combination heater and humidifier is sent through the inhalant tube to the patient's lungs. During its passage through the inhalant tube, the inhalant gas radiates heat and loses temperature. If the temperature of the combination heater and humidifier is kept higher than that of the lungs, the temperature of the inhalant gas often falls below 31° C. at the outlet of the connector on the patient's side. To preclude the fall of temperature of the inhalant gas in the connector, there is adopted a device utilizing a heater inside the exhalant tube or on the outer periphery of the exhalant tube. This device has a disadvantage that the addition of the heater increases the cost of equipment, the temperature control of the heater is difficult, and the heater itself is not easily cleaned and sterilized.

Further, near the patient's mouth, two tubes are disposed through the medium of the connector. Especially when the inner pressure of the circuit and the temperature of the inhalant gas are monitored near the mouth, the various devices which are required for the monitoring complicate the portion of the construction close to the mouth to a great extent and annoy the patient notably. The devices themselves are handled with difficulty.

As breathing circuits mainly used for anesthesis, the Payne circuit and the F circuit have been known in the art (Japanese Published Unexamined Patent No. 150,893/1979), for example.

These circuits have a common construction wherein a straight inner tube and a usually corrugated outer tube are coaxially assembled in a two-wall structure, with the interior of the inner tube intended as an inhalant circuit and the space between the outer tube and the inner tube as an exhalant circuit. One end of the coaxial tube on the patient side is connected to a connector which is provided with an inlet and an outlet. The other ends of the outer tube and inner tube on the anesthetizer side are fastened to outlets of a manifold. Through the inner communicating hole and the outer communicating hole of the manifold, the anesthetic gas from the anesthetizer is circulated.

Owing to the use of the coaxial tube, the circuits of this class are easy to handle. Compared with the aforementioned system in which the inhalant tube and the exhalant tube are disposed as two independent passages, the circuit of interest permits a reduction in the heat loss of the inhalant gas because the outer tube exists around the periphery of the inner tube serving as a path for the inhalant gas and further because the exhalant gas flows in close contact with the periphery of the inner tube.

This circuit is provided with neither an exhalation valve nor a nebulizer. Owing to the use of the coaxial tube, it does not permit insertion of such devices at points falling halfway along the length of the duct. It has a disadvantage, therefore, that it limits the types of respirators which are effectively usable with the circuit.

As described above, the inhalant gas which is delivered to the patient's lungs is desired to be at a temperature falling below the temperature of the lungs, preferably in the range of 32° to 35° C. In the case of a circuit which uses a coaxial tube constructed as described above and which has a combination heater and humidifier connected to the coaxial tube, the inhalant gas which has been treated by the combination heater and humidifier and readied for delivery to the lungs is likewise desired to have a temperature below the temperature of the lungs. This temperature condition counts much because the possibility of the temperature of the inhalant gas being abruptly raised by an unexpected trouble, the temperature being gradually heightened during a prolonged delivery of the inhalant gas, and the inhalent gas being delivered to the lungs at a temperature higher than the temperature of the lungs will be completely eliminated when the condition is fulfilled. Besides, since the difference between the temperature of the inhalant gas and the room temperature is narrowed, the loss of heat or the value of temperature drop is decreased and the amount of moisture suffered to form dew is also decreased.

It has been ascertained, however, that when a coaxial tube is formed in an ordinary structure and an inhalant gas heated by a combination heater and humidifier to a temperature lower than the temperature of the patient's lungs is forwarded so that, upon arrival at the patient's mouth, the gas may have a temperature in the range of 32° to 35° C., the circuit of interest fails to give a perfect solution to the problem of heat loss which the inhalant gas undergoes on route to the patient's mouth.

To be more specific, the magnitude of heat loss involved in the circiut of interest is decisively small as compared with the circuit using two independent tubes and it is also small as compared with the circuit involving delivery of the inhalent gas at a temperature higher than the temperature of the lungs. The decrease in the magnitude of heat loss, however, is not necessarily quite satisfactory. When the length of the coaxial circuit is increased, for example, the temperature drop of the inhalant gas during its travel through the circuit to the patient's mouth is increased. When the circuit is used for a prolonged period of artificial respiration, the amount of moisture suffered to form dew is also increased.

Moreover, the temperature range in which the combination heater and humidifier is allowed to be heated for the purpose of delivering to the patient the inhalant gas at an optimum temperature of 32° to 35° C. is so narrow that when the temperature of the combination heater and humidifier is varied, there is a possibility that the inhalant gas will be delivered to the patient's mouth at a temperature falling outside the optimum range.

Japanese Published Unexamined Patent No. 150,893/1979 discloses an embodiment wherein an inner tube is semi-fixed inside the portion of a connector on the patient side through the medium of a spacer. It has been ascertained that in this embodiment, the aforementioned disadvantage is not overcome because the inner tube comes off the spacer and the entire circuit elongates when the inevitably increased resistance of the gas passage and decrease of lung compliance cause the inner pressure of the circuit to rise to the order of more than some tens of cm of $H_2O$ column.

Further in the circuit of the construction described above, since the inner tube used therein is a normally straight tube, the gas passage enclosed therein may possibly be collapsed heavily by a bend in the tube.

Furthermore, for the sake of the breathing circuit, it is desirable for a nebulizer to be inserted in the inhalant circuit as described above. For the nebulizer to retain its efficiency intact in the delivery of aerosol, it is desired to be disposed at a position closer toward the patient. In the circuit of the construction described above, since the circuit is formed in a coaxial structure as indicated above, it is difficult for the nebulizer to be integrally inserted and disposed completely within the circuit. No construction incorporating a nebulizer within a breathing circuit has ever been developed to date.

British Patent Publication No. 2,029,703A discloses an anesthetic circuit wherein an inner tube and an outer tube which are both corrugated tubes are coaxially assembled in a two-wall structure and both the inner and outer tubes are fixed simultaneously to a connector on the patient side. In the circuit of this construction, collapse of the circuit does not frequently occur because the inner tube has a corrugated wall.

In this case, as concerns the overall elongation of the circuit as a whole, since both the outer tube and the inner tube are fixed to the connector on the patient side, the inner tube offers resistance to and restricts the elongation of the outer corrugated tube when the inner pressure of the circuit is increased. Compared with the circuit of the previous construction, therefore, this circuit has lower overall elongation and less dead space. A coaxial tube constructed by coaxially assembling two corrugated tubes of different diameters in accordance with the disclosure of British Patent Publication No. 2,029,703A mentioned above and in conformity to the conventional technique has shown a still large overall circuit elongation and, particularly for use as a breathing circuit, has proved unsatisfactory in terms of dead space and constancy of performance.

Even in the circuit of this construction, integral insertion of a nebulizer in a disposition capable of enhancing the efficiency of aerosol delivery is difficult. This insertion has not yet been materialized in any of the ducts developed to date.

An object of this invention, therefore, is to provide a novel breathing circuit.

Another object of this invention is to provide a breathing circuit of the construction of a coaxial tube which suffers from far less heat loss than the conventional circuit of the same function.

Yet another object of this invention is to provide a breathing circuit which has a simple, compact structure and an easily operated mechanism, entails no heavy heat loss, produces no large amount of moisture for dew formation, offers no heavy inhalant and exhalant resistance, and excels in the versatility of a respirator.

SUMMARY OF THE INVENTION

The objects described above are accomplished by provision of a breathing circuit which comprises a coaxial tube type main tube comprising a flexible inner tube defining an inhalant circuit and a corrugated outer tube having a larger average wall thickness than the aforementioned inner tube, disposed around the periphery of the inner tube, and defining an exhalant circuit in conjunction with the periphery of the inner tube; and an inner tube retaining member disposed at least at one end of the aforementioned coaxial tube type main tube so as to keep the inner tube and the outer tube at a fixed distance from each other.

BRIEF DESCRIPTION OF THE DRAWING

FIG. 1 is a cross section illustrating one embodiment of the breathing circuit according to the present invention, FIG. 2 is an enlarged side view of an inner tube retaining member, FIG. 3 is an enlarged front view of the inner tube retaining member, FIG. 4 is a cross section taken along the line IV—IV in the diagram of FIG. 3, FIG. 5 is a cross section taken along the line V—V in the diagram of FIG. 3, FIG. 6 is an enlarged cross section of a manifold, FIG. 7 is a cross section for illustrating the dimensional relation between the smaller diameter and the larger diameter of a corrugated tube, FIG. 8 is a side view illustrating one embodiment of the corrugated tube, FIG. 9 is a cross section taken along the line IX—IX in the diagram of FIG. 8, FIG. 10 is a side view illustrating another embodiment of the corrugated tube, FIG. 11 is a cross section taken along the line XI—XI in the diagram of FIG. 10, FIGS. 12–16 are side views illustrating other embodiments of the corrugated tube, FIG. 17 is a cross section illustrating another embodiment of the circuit according to the present invention, FIG. 18 is an enlarged cross section of a coaxial tube type manifold to be used in the circuit of the present invention, FIG. 19 is a cross section taken along the line XIX—XIX in the diagram of FIG. 18, FIG. 20 is a cross section taken along the line XX—XX in the diagram of FIG. 18, FIG. 21 is a cross section illustrating yet another embodiment of the circuit of the present invention, FIG. 22 is a plan view of the duct of FIG. 21.

PREFERRED EMBODIMENT OF THE INVENTION

Figure 23:
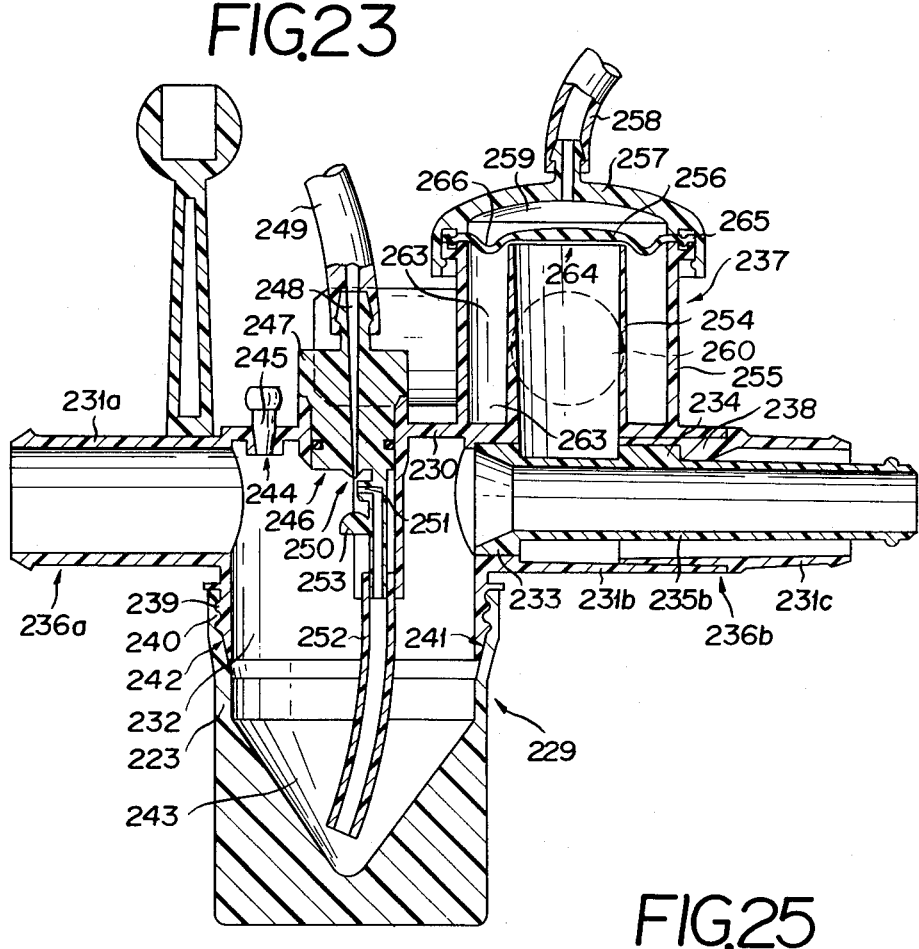
FIG. 23 is an enlarged cross section of another embodiment of the manifold of this invention.
Figure 24:
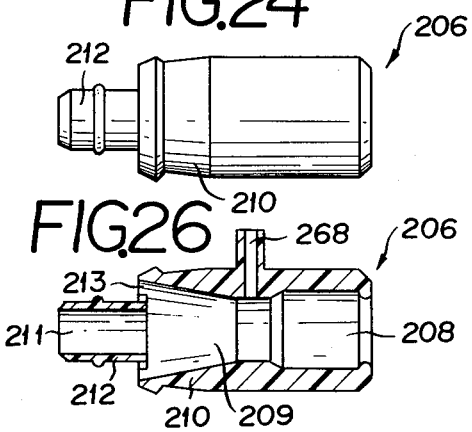
FIG. 24 is an enlarged side view illustrating another embodiment of the inner tube retaining member.
Figure 25:
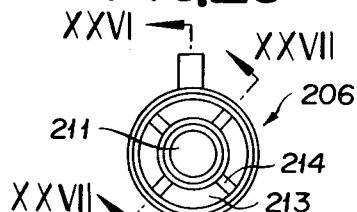
FIG. 25 is an enlarged front view of the inner tube retaining member.
Figure 26:
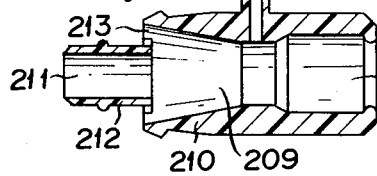
FIG. 26 is a cross section taken along the line XXVI—XXVI in the diagram of FIG. 25.
Figure 27:
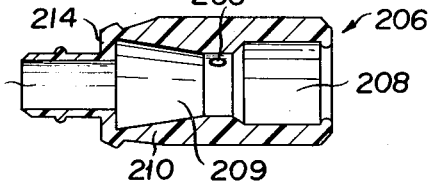
FIG. 27 is a cross section taken along the line XXVII—XXVII in the diagram of FIG. 25.

As illustrated in FIG. 1, the breathing or anesthetic circuit of this invention (hereinafter, referred to collectively as "breathing circuit") comprises a coaxial tube type main tube 5 comprising a flexible inner tube 2 forming an inhalant circuit 1 and a corrugated outer tube 4 of a substantially equal length disposed around the periphery of the inner tube and defining an exhalant circuit 3 in conjunction with the inner tube 2, with one of the opposite ends thereof connected to an inner tube retaining member 6 adapted to keep the inner tube 2 and the outer tube at a fixed distance from each other and the other end connected to a manifold 7. An axis of the inner tube does not always coincide with that of the outer tube, and "coaxial" implies said condition.

The outer tube 4 and the inner tube 2 to be used in the circuit are required to be such that the average wall thickness of the inner tube is smaller than that of the outer tube. If the average wall thickness of the inner tube is greater than or equal to that of the outer tube, the heat loss which occurs when the inhalant gas is heated to a temperature lower than the temperature of the lungs disadvantageously increases. This fact will become apparent from the experiments described afterward.

In this case, the loss of heat suffered by the inhalant gas heated to below the temperature of the lung is lightened so far as the average wall thickness of the inner tube is smaller than that of the outer tube. This reduction of heat loss is most advantageously effected by limiting the average wall thickness of the inner tube to within the range of 20 to 90% of the average wall thickness of the outer tube.

As regards the average wall thicknesses of the inner and outer tubes which are subject to the restriction mentioned above, they are not particularly limited so far as they fall within the ranges commonly accepted. Desirably, the average wall thickness of the inner tube is in the range of 0.2 to 1 mm and that of the outer tube particularly in the range of 0.4 to 1.5 mm.

In accordance with the present invention, the breathing circuit is formed by solely using a coaxial tube 1 as illustrated in FIG. 1 or by joining a multiplicity, generally two, of such coaxial tubes connected through the medium of a prescribed manifold as illustrated in FIG. 17.

In this case, it is essential that in the sole coaxial tube or in each of the multiplicity of coaxial tubes, the outer tube 4 should possess a greater average wall thickness than the inner tube 2 and that the outer tube should possess a corrugated wall. Possible collapse of the circuit due to the phenomenon of kinking is lessened when the requirement is satisfied.

In contrast, the inner tube 2 has a smaller diameter and is less susceptible to the phenomenon of kinking. The inner tube, therefore, may possess a corrugated wall or straight wall insofar as it is flexible. Where a plurality of inner tubes 2 are used, they may possess mutually different diameters only if their average wall thicknesses are smaller than the average wall thicknesses of the corresponding outer tubes 4.

Besides the conditions mentioned above, the inner tube 2 and the outer tube 4 to be used in the breathing circuit are not subject to any particular restrictions. Other conditions of these tubes, therefore, may be suitably selected from the respective ranges accepted commonly in the art. For example, the materials of which the inner tube 2 and the outer tube 4 are made may be equal to or different from each other. They can be suitably selected from varying known materials available for the manufacture of flexible tubes. Examples of such materials include polyethylene, polypropylene, polyamide, polyvinyl chloride, polyesters represented by polyethylene terephthalate and polyurethane. The inside diameters of the inner tube 2 and the outer tube 4 may be roughly in the ranges of 8 to 20 mm and 20 to 30 mm respectively. The ratio of the inside diameters may be roughly in the range of 1:1.5 to 1:2.5. In the case of a corrugated tube, the difference between the largest outside diameter and the smallest inside diameter may be roughly in the range of 1.5 to 5 mm. The radius of curvature of each of the ridges of corrugation may be fixed roughly in the range of 0.5 to 1.5 mm. The length of the coaxial tube 5 may be roughly 0.7 to 1.5 m.

At the leading end of the coaxial type main tube 5, there is provided the inner tube retaining member 6 which serves to keep the inner tube 2 and the outer tube 4 at a fixed distance from each other. The inner tube retaining member 6 may be formed of protuberances which are raised radially relative to the axis of the inner tube 2 in a plurality of directions, three directions, for example, to the extent of substantially adjoining the inner surface of the outer tube. A connector of the construction illustrated in FIGS. 2 through 5 is preferably used as the inner tube retaining member 6. The inner tube retaining member 6 is in the form of a outer tube portion 10 provided at one end thereof with an air hole 8 and at the other end thereof with an outer tube fitting end 9. Inside the outer tube fitting end 9, an inner tube fitting portion 12 provided with an inner tube fitting end 11 is coaxially disposed. Between the inner tube fitting portion 12 and the outer tube portion 10, at least one, preferably a plurality of openings 13 are formed. Through the portions excluding these openings 13, the inner tube fitting portion 12 and the outer tube portion 10 are connected to each other. In other words, the inner tube fitting portion 12 is connected to the outer tube portion 10 with columnar pieces 14 projected outwardly at fixed intervals radially from the axial line. They are usually molded integrally in a one-piece construction. The openings 13 may be formed circularly, elliptically, or otherwise as freely selected. They are generally formed integrally with any of the synthetic resins mentioned above. The inner tube fitting portion 12 is generally made to protrude from the leading end of the outer tube fitting end 9 with a view to facilitating the fitting of the inner tube 2 of the coaxial main tube 5.

To the outer tube 10 and the inner tube fitting member 12 of this inner tube retaining member 6, the outer tube 4 and the inner tube 2 are respectively fitted. The fitting is accomplished by simply inserting these tubes around the respective fitting ends and fastening the fitted end of the outer tube 4 with application of pressure to suit the occasion. It is because the outer tube 4 and the inner tube 6b are fastened to the inner tube retaining member 6 that the expansion of the whole circuit is decreased to an extremely small extent.

The one end of the other coaxial main tube 5 is connected to the forked pipe 7. The forked pipe 7 is provided with a side pipe 16 forming an outer tube communication hole 15 and a main pipe 18 forming an inner tube communication hole 17. The other end of the main pipe 18 forms an outer tube fitting member 19. Inside the outer tube fitting member 19, an inner tube fitting member 20 is coaxially disposed. One end of the inner tube fitting member 20 forms an opening and the other end thereof continues into the inner wall of the main pipe 18 to close the outer tube fitting member 19. All these components are molded of any of the aforementioned synthetic resins. The outer tube communication hole 15 of the side pipe 16 communicates with a cavity 21 which is formed between the outer tube fitting member 19 and the inner tube fitting member 20. With the forked pipe 7 of the construction described above, the outer tube 4 and the inner tube 2 of the coaxial main tube 5 are fitted fast respectively to the outer tube fitting member 19 and the inner tube fitting member 20.

Where the outer tube 4 and the inner tube 2 are both flexible corrugated tubes of a circular cross section, for example, it is desired that they should be assembled in such a structure that the inner tube 2 has a smaller ratio of elongation than the outer tube 4. The ratios of elongation can be easily measured by applying a fixed inner pressure (of the order of 30 to 100 cm $H_2O$) to each of the inner tube 2 and the outer tube 4 in use. Advantageous results are obtained when the ratio of elongation of the inner tube 2 divided by that of the outer tube 4 gives a quotient not exceeding 0.8.

Construction of a coaxial tube such that the ratio of elongation of an inner corrugated tube 2 is smaller than that of an outer corrugated tube 4 can be embodied in different manners.

In a first embodiment, the ratio of elongation of the inner tube 2 can be made smaller than that of the outer tube 4 by designing the wall thicknesses of the inner and outer tubes so that the difference ($\Phi - \phi$) between the outside diameter at the peak of each ridge (indicated by $\Phi$ in FIG. 7) and the outside diameter at the bottom of each groove (indicated by $\phi$ in FIG. 7) is smaller in the inner tube than in the outer tube. In this case, the aforementioned difference ($\Phi - \phi$) between the outside diameter at the peak of ridge and that at the bottom of groove can be obtained by measuring the outside diameters of a tube under application of no load and comparing the values found. This difference ($\Phi - \phi$) governs the ratio of elongation of the corrugated tube as a primary factor. Required differentiation between the ratios of elongation of the inner tube and outer tube can be advantageously accomplished by fulfilling the aforementioned relation of the two corrugated tubes in terms of this difference. Advantageous results are obtained when the division of the difference ($\Phi - \phi$) of the inner tube by the difference ($\Phi - \phi$) of the outer tube gives a quotient falling in the range of 0.20 to 0.95, preferably 0.4 to 0.8. Generally the difference ($\phi - \phi$) of the outer tube may be roughly in the range of 1.5 to 4 mm.

In a second embodiment, the ratio of elongation of the inner tube 2 can be made smaller than that of the outer tube 4 by designing the corrugations of the inner and outer tubes so that the radii of curvature (indicated by r in FIG. 7) at the extremities of ridges and grooves of the corrugated wall, i.e., the radii of curvature near the peak of each ridge and the bottom of each groove, are smaller in the inner tube than in the outer tube. In this case, these radii of curvature at the extremities of ridges and grooves of a corrugated tube can be found by measuring radii of curvature of the inner wall surface and the outer wall surface of the tube while the tube is held under application of no load. Advantageous results are obtained when the radius of curvature (r) at the extremity of ridge and groove in the inner tube divided by the radius of curvature (r) at the extremity of ridge and groove in the outer tube gives a quotient falling in the range of 0.15 to 0.95, preferably 0.3 to 0.7.

The aforementioned difference ($\Phi - \phi$) between the ridge and bottom diameters of the corrugated tube and the radii of curvature at the extremities of ridges and grooves are two separator factors which govern the ratio of elongation of the corrugated tube. Although the first and second embodiments described above may be independently adopted in making the ratio of elongation of the inner tube smaller than that of the outer tube, combined adoption of the two embodiments permits the inner tube to assume smaller difference ($\Phi - \phi$) and radii of curvature than the outer tube and, accordingly, affords more advantageous results.

In a third embodiment in addition to the foregoing two embodiments, without reference to conformity thereof with the first and second embodiments, the ratio of elongation of the inner tube 2 may be made smaller than that of the outer tube 4 by forming the inner tube 2 and the outer tube 4 with different materials, specifically by forming the inner tube 2 with a material of higher rigidity and the outer tube 4 with a material of lower rigidity. In this case, the rigidity of material can be compared by the scale of Shore hardness. Advantageous results are obtained when the two values of Shore hardness found for the inner and outer tubes give a difference roughly in excess of 15.

For the sake of this difference of rigidity, the outer tube may be formed of polyethylene, ethylene-vinyl acetate copolymer, polyvinyl acetate, polyurethane or polyvinyl alcohol. In contrast to such material of the outer tube, the inner tube may be formed of a material of higher rigidity to be suitably selected from among polyethylene, polypropylene, polyvinyl chloride, polyamide, and polyesters, for example. From the standpoint of ease of fabrication and cost of manufacture, it is particularly advantageous to form the outer tube and the inner tube with two grades of polyethylene differing in rigidity from each other.

In the third embodiment, the differences of the inner tube and the outer tube in terms of the factors, ($\Phi - \phi$) and r, respectively of the first and second embodiments does not matter.

Besides the embodiments described above, the ratio of elongation of the inner tube 2 can be made smaller than that of the outer tube 4 by providing the corrugated tube with means capable of restricting the expansion and contraction of the tube in the axial direction. In the corrugated tube illustrated in FIG. 8, for example, freely expansible ridges 32 are provided as regularly spaced by a fixed pitch throughout the entire length of the tube and one flat, straight strip 33 designed to limit the expansion and contraction of the tube is provided on the periphery of the tube as merged in the ridges. As illustrated in FIG. 9 which represents a cross section of the tube taken along the line IX—IX in the diagram of FIG. 8, the distance in the radial direction of the straight strip 33 from the axis of the corrugated tube equals the radius of the ridge 35 of the tube. This equality is not critical. The distance in the radial direction of the straight strip 33 from the axis of the corrugated tube can be freely varied within the range which has the radius of the corrugation 32 at the ridge 35 as its upper limit and the radius at the groove 34 as its lower limit. In this case and in any of the cases to be cited herein below, the width of the straight strip 33 is not desired to be increased so much as to deprive the corrugated tube 31 of its flexibility excessively.

The corrugated tube 41 illustrated in FIG. 10 has freely expansible ridges 42 regularly spaced at a fixed pitch throughout the entire length of the tube and straight strips 33 provided on the periphery of the tube in such a manner that the strips, taken individually, are staggered in the circumferential direction by a fixed angle of 90° and, taken collectively, are laid unbrokenly over the entire length of the tube. FIG. 11 represents a cross section taken along the line XI—XI in the diagram of FIG. 10. It is noted from FIG. 11 that the distance in the radial direction of the straight strip 43 from the axis of the corrugated tube is equal to the radius of the ridge 43 of the corrugation 42 and that the cross section is taken in the groove 44.

The corrugated tubes 51, 61 illustrated respectively in FIG. 12 and FIG. 13 are provided with freely expansible ridges 52, 62 regularly spaced by a fixed pitch throughout the entire length of the tubes. One smooth-faced strip 56 is spiralled on the tube of FIG. 12 and two smooth-faced strips 66 are parallelly spiralled on the tube of FIG. 13 respectively as merged into the ridges 52, 62.

The corrugated tubes 71, 81 illustrated respectively in FIG. 14 and FIG. 15 have corrugated portions each containing a plurality of ridges 72, 82, namely two ridges in the tube of FIG. 14 and three ridges in the tube of FIG. 15, and straight cylindrical portions 77, 87 provided alternately. In these corrugated tubes, the straight cylindrical portions 77, 87 constitute means for restricting the expansion and contraction of the tubes. In the corrugated tube having corrugated portions and straight cylindrical portions 97 provided alternately as illustrated in FIG. 16, straight strips 93 extended in the axial direction across corrugated portions and/or smooth-faced strips 96 spiralled on the corrugated portions may be raised to a height between the height of the ridges and the height of the grooves respectively of the corrugated portions so as to serve as means for restricting the expansion and contraction of the tube in addition to the straight cylindrical portions.

The foregoing illustrated embodiments are only typical examples of corrugated tubes of limited expansibility to be used in the respiratory duct of the present invention. Naturally, any other construction may be adopted so far as it is capable of providing effective restriction of the expansion and contraction of the corrugated portions formed on the tube body. The constructions of corrugated tube conforming to this invention are not limited to those illustrated above. Constructions having spiral ridges in corrugated portions are also embraced by this invention.

It has been ascertained that particularly in a corrugated tube containing smooth-faced cylindrical portions, the relation between the length, l, in the axial direction of the smooth-faced cylindrical portions and the number of ridges in the individual corrugated portions ought to fall within a specific range in order to accomplish the object of the duct. The smooth-faced cylindrical portions are required to have a length of not more than 30 mm. The relation must satisfy the formula, $p<l<np$, wherein n ($n \geqq 2$) stands for the number of ridges in the corrugated portions. The typical constructions illustrated in FIG. 14 and FIG. 15 naturally satisfy this relation.

Another embodiment of this invention illustrated in FIG. 17 predominately comprises a first coaxial tube type main tube 105a, a coaxial tube type manifold 122, a second coaxial tube type main tube 105b, and an inner tube retaining member 106 arranged in serial connection. When necessary, the first coaxial tube type main tube 105a is connected to a forked tube 107.

The first and second coaxial tube type main tubes 105a, 106b respectively comprise flexible inner tubes 102a, 102b each forming an inhalant circuit and corrugated outer tubes 104a, 104b each defining an exhalant circuit in conjunction with the aforementioned inner tubes. The inner tubes 102a, 102b are generally smooth-faced or corrugated flexible tubes having a circular cross section. Particularly they are desired to be smooth-faced flexible tubes, because such tubes produce no heavy elongation. The outer tubes 104a, 104b are generally corrugated flexible tubes having a circular cross section. They serve to lessen the possibility of the circuit being collapsed under an external force. The inner tubes and the outer tubes which form the coaxial tube are the same as those described above.

In the first and second coaxial type main tubes 105a, 105b constructed as described above, the inner tubes 102a, 102b are used as inhalation paths and the spaces intervening between the inner tubes 102a, 102b and the outer tubes 104a, 104b are used as exhalation paths.

In the manifold 122, as illustrated in FIGS. 18 to 20, outer tubes 131a, 131b are projected from the lateral wall of a cap 130 of the nebulizer 129 and are allowed to communicate with a cavity 132 in the nebulizer. Inside the outer tubes 131a, 131b, inner tubes 135a, 135b provided at the inner ends thereof each with a flange 133 and near the outer ends thereof each with spacers projected outwardly from at least two positions, usually from three positions, for example, and radially relative to the axes of the outer tubes 131a, 131b, and adapted to adjoin the inner walls of the aforementioned outer tubes are coaxially inserted in such a manner that the aforementioned flanges 133 will come into contact with the outer tubes 131a, 131b near the lateral wall of the cap 130. Thus, the outer tubes 131a, 131b and the inner tubes 135a, 135b form coaxial tubes 136a, 136b. If the inner tubes 135a, 135b are held in the outer tubes 131a, 131b by the flanges 133 and spacer 134, it is extremely easier to produce than one which is molded integrally with the manifold 122. The spacers 134 are in the form of blades disposed parallelly to the axial lines of the coaxial tubes, for example. They may be in the form of columns or some other similar objects on condition that they should refrain from closing the exhalation paths to be formed between the outer tubes 131a, 131b and the inner tubes 135a, 135b. Optionally, in the outer tube 131b which is provided with an exhalation valve 137 described more fully in a later paragraph, an outer tube connector 131c having spacers 138 resembling the aforementioned spacers and projected inwardly radially relative to the axial line may be inserted. By the flanges 133 provided at the inner ends of the inner tubes 135a, 135b are described above, the exhalation paths formed between the outer tubes 131a, 131b and the inner tubes 135a, 135b are shut off the nebulizer 129. The inner tubes 135a, 135b are allowed to communicate with the cavity in the nebulizer 129.

The nebulizer 129 may be formed integrally in a one-piece construction. Generally, it comprises a cap closing the inner ends of the outer tubes 131a, 131b of the manifold 122 comprising the coaxial tubes 136a, 136b and communicating with the inner ends of one inner tube 15a and the other inner tube 135b and a container 123 fitted freely detachably to the cap 130 as illustrated in FIG. 18. The connection between the cap 130 and the container 123 may be made in any of the forms available. Generally, it is accomplished by means of matched screws 139, 140. Particularly this connection is obtained desirably by providing the screw 139 at the portion of the cap 120 destined for contact with the container and a fitting part 141 of a tapered surface at the leading end of the screw 139 and also providing the screw 140 at the portion of the container 123 destined for contact with the cap and a fitting part 142 of a tapered surface at the inner-most recess of the screw 140. The screws are formed in ample lengths such that as the cap 130 is helically advanced into the container 123, the respective fitting parts 141, 142 of tapered surface will be brought into intimate engagement with each other. The container 123 forms a reservoir 143 for a medication or water. The cap 130 is provided at the top thereof with a port 144 for the introduction of a medicinal solution. This port 144 is normally closed with a stopper 145 provided rubber position. In this case, even if the stopper is not removed, the medicinal solution can be introduced by inserting a needle of a syringe into a rubber portion, and thus contamination in the nebulizer by air can be prevented. Also at the top of the cap 130, a release nozzle port 146 is formed. The release nozzle port 146 is fitted with an O ring, for example, and permits insertion of an outer pressure release nozzle 147 which is provided at the lower portion thereof with a venturi mechanism. The inlet 148 to this nozzle 147 communicates with an outer pressure inlet tube 149. The lower end of this inlet 148 forms an outer pressure release outlet 30. Near the leading end of the release outlet 150 is disposed a medication spray nozzle 151. This nozzle 151 communicates with a tube 152. At a still lower portion of the aforementioned release outlet 150 is provided a baffle member 153.

In the preferred embodiment of FIG. 18, the inner surface at the upper end of the container 123 is fitted on the outer surface at the lower end of the cap 130. For the purpose of this engagement, their respective fitting parts 141, 142 of tapered surface are formed below the respective screws 139, 140. Optionally, the screws 139, 140 and the fitting parts 141, 142 of tapered surface may change their places.

The exhalation valve 137 is disposed on the outer tube 131b, namely the one on the inhalation inlet (patient) side of the two outer tubes closed and separated from each other by the nebulizer 129 as illustrated in FIGS. 18 to 20. The exhalation valve 137 comprises an inner cylinder 154 disposed communicably with the outer tube 11b and an outer cylinder 155 disposed coaxially with the inner cylinder 154, not allowed to communicate with the outer tube 131b, and shut off the ambient air. The open edges of the inner and outer cylinders 154, 155 are sealed tightly with a valve body, i.e., a diaphragm 156. This diaphragm 156 is fastened to the circumferential edge of the outer cylinder 155 by means of a cap 157. The cavity enclosed between the cap 157 and the diaphragm 156 communicates with the tube 158 and forms a compression chamber 159 to which is supplied an actuating pressure of the exhalation valve for closing the exhalation path and an actuating pressure of the exhalation valve to cause the positive end-expiratory pressure through the tube 158 to act upon the outer surface of the diaphragm 156 in case of inhalation. In the lateral wall of the outer tube 155, a port 160 opens. On the other a port 161 opens in the lateral wall of the other outer tube 131a which is closed by the nebulizer 129. These ports 160, 161 are interconnected by a by-pass tube 162. The exhalation forwarded from the patientside as described more fully at a later paragraph finds its way through the outer tube 131b to the inner cylinder 154 of the exhalation valve 137, pushes the diaphragm 156 upwardly, reaches the cavity 163 formed between the outer cylinder and the inner cylinder 154, and further advances through the port 160 of the outer cylinder 155, the by-pass tube 162, and the port 161 to the interior of the outer tube 131a. The above mentioned valve body is not limited to the diaphragm 156, but any member which closes the open edge of the inner cylinder when inhalation occurs and opens it when exhalation occurs can be used.

The manifold 122 containing the outer tube, the inner tube, the nebulizer, and the exhalation valve may be made of the same material as the coaxial type main tube. Otherwise, it may be made of polyacetal, an ABS resin, etc. The diaphragm 156 is made of natural rubber or synthetic rubber such as chloroprene rubber, SBR, silicone rubber, etc. for example.

In the exhalation valve 137, the cap 157 which fastens the diaphragm 156 to the upper edge of the outer cylinder 155 is fixed so as to cover the open edge 164 of the inner cylinder 154 and give rise to the compression chamber 39 on the diaphragm 156. In this case, the diaphragm 156 is fixed by having the periphery 165 thereof pinched between the outer cylinder 155 and the cap 157 in such a manner that the peripheral face of the inner cylinder of diaphragm 156 is separated by a gap of at least 0.2 mm, preferably 0.2 to 0.5 mm, from the open edge 164 of the inner cylinder while the compression chamber 159 positioned thereon is free from pressure. The central portion of the diaphragm 156, namely the portion corresponding to the inner cylinder 154, has a wall thickness at least twice the wall thickness of the peripheral portion falling outside the inner cylinder 154. In the portion of the diaphragm falling outside the inner cylinder 154, an annular groove 166 is formed.

A balloon-shaped valve body may be provided at an outlet of air for compression of the cap 157 instead of the diaphragm, which can close the open edge 164 of the inner cylinder 154 by expansion thereof.

FIGS. 21 and 22 illustrate yet another embodiment of this invention. In this breathing circuit, an inner tube retaining member 206 is connected to one end of a coaxial tube type tube 205 formed of an outer tube 204 and the inner tube 202 and a manifold 222 fitted with an exhalation valve 237 and a nebulizer 229 is connected to the other end of the coaxial tube type tube 205. Consequently, the interior of the inner tube 202 communicates with the void in the nebulizer 229 and the exhalant circuit defined by the outer tube 204 and the inner tube 202 communicates with the exhalation valve 237. A corrugated or smooth-faced flexible inhalant gas lead tube 275 is connected to the remaining end of the manifold 222 and a corrugated or smooth-faced flexible exhalant gas lead tube 276 connected at the port 260 to the exhalation valve 237. The inner tube 207, the outer tube 204, and the coaxial tube type tube 205 to be used herein are the same as those described above.

In the manifold 222 to be used herein, as illustrated in FIG. 23, outer tubes 231a, 231b are projected out of the lateral walls of a cap 230 of the nebulizer 229 and the interiors thereof are consequently allowed to communicate with the void 232 in the nebulizer. Inside the outer tube 231b, an inner tube 235b which is provided at adjacent one end thereof with a flange 233 and at the other end thereof with spacers raised outwardly therefrom radially relative to the axial line of the outer tube 231b at two points at least, at three points, for example, until intimate contact with the inner wall surface of the outer tube is coaxially inserted so that the flange 233 falls on the outer tube 231b adjacent the lateral wall of the cap 230. Thus, the outer tube 231b and the inner tube 235b form a coaxial tube 236b. The other outer tube 231a does not form any coaxial tube. The interior of the outer tube 231a communicates with the void in the cap 230.

The exhalation valve 237 is provided within the outer tube 231b which forms part of the aforementioned coaxial tube. The lateral wall of an outer cylinder 255 which forms the aforementioned exhalation valve 237 has an opening. In all other respects, the construction of this tube is roughly the same as that illustrated in FIGS. 18–20. The numeric symbols of FIG. 23 which equal the sums of numeric symbols of FIGS. 18–20 and 100 denote the same parts as the latter numeric symbols.

The inner tube retaining member 206 to be used in the present embodiment as illustrated in FIGS. 24–27 is similar to that illustrated in FIGS. 2–5. An outer tube portion 210 of the inner tube retaining member is provided with a monitor hole 268. The inner tube retaining member 206 is provided, when necessary, at the leading end thereof with a freely rotatable mouth piece (L-shaped tube) 269. In FIGS. 24–27, the numeric symbols which equal the sums of numeric symbols of FIGS. 24–27 and 200 denote the same parts as the latter numeric symbols.

Now, the use of the breathing circuit of this invention constructed as illustrated above will be described below. In the case of the duct illustrated in FIGS. 1–6, the hole 17 of the forked tube 7 communicating with the inner tube is connected via a lead pipe to a ventilator or an anesthetizer (not shown) and the hole 15 of the forked tube 7 communicating with the outer tube is connected to an exhalant valve (not shown) which is provided in the ventilator or anesthetizer. A mouth piece may be connected to the inner tube retaining member 6 when necessary. In the circuit of this construction, the inhalant gas or anesthetic gas is forwarded through the inner tube and fed through the mouth piece into the patient's lungs and the exhalant gas is discharged through the exhalant circuit defined by the outer tube and the inner tube.

In the case of the circuit illustrated in FIGS. 17–20, the needle of a syringe containing a medicinal solution is pierced through a stopper 145 provided rubber portion to inject the medicinal solution into the nebulizer 129. The mouth piece 169 is set in position. Then, the inhalant gas supplied from the ventilator flows through the tube 170, the inner tube communicating hole of the forked tube 107, and the inner tube 102a of the first coaxial tube type main tube 105a, reaches the interior of the inner tube 135a of the manifold 122, and finds its way into the nebulizer 129. The external pressure is led through an inlet tube 149 into an external pressure nozzle 147 and spurted out intermittently, for example, through a spurting mouth 150. The negative pressure which is generated by the jet of air applied to the outlet of a spray nozzle 151 attracts the medicinal solution through a lead tube 152, with the result that the medicinal solution will be sprayed in the form of aerosol by the so-called Venturi effect. A baffle member 153 is disposed in the direction in which the jet of air is spurted. The aerosol of medicinal solution carried by the jet of air collides with this baffle member 153 and is scattered. The particles of the medicinal solution are consequently divided further and uniformized. The jet of air to be supplied to the spurting mouth 160 is generally formed of the same gas as used for delivery as an inhalant gas to the patient. And it is produced intermittently only during inhalation. The medicinal solution may be poured in through a medicinal solution feed mouth 144 which is opened by the removal of the stopper 145.

The inhalant gas which is mixed with the aerosol within the nebulizer 129 is fed through the inner tube 135b of the manifold, the inner tube 102b of the second coaxial tube type main tube 105b, the inner tube retaining member 106, and the mouth piece 169 into the tracheal catheter, for example, on the patient side (not shown) and put to use in artificial respiration. Where the administration of the medicinal solution in the form of aerosol is not called for, the forwarding of the inhalant gas is carried out similarly to effect desired artificial respiration without involving the introduction of external pressure through the inlet tube 29.

The exhalant gas discharged from the patient's lungs is forwarded through the mouth piece 169 and the inner tube retaining member 106, then passed through the opening of the inner tube retaining member and the exhalant circuit formed between the outer tube 104b and the inner tube 102b of the second coaxial tube type main tube 105b, and led into the inner cylinder 154 of the exhalation valve 137 via the void defined by the outer tube 131b and the inner tube 135b of the manifold 122.

In the exhalation valve 137, at the inhalation step, air of relatively high pressure is introduced through a lead tube 158 into a pressure chamber 159 to press a diaphragm 156 tightly against an edge of the inner cylinder and shut off tightly the flow path of the inner cylinder 154. During the period of exhalation which follows the delivery of the inhalant gas, the exhalant gas pushes the diaphragm 156 upwardly and finds its way into a cavity 163 formed between the outer cylinder 155 and the inner cylinder 154. From this cavity 163, the exhalant gas is forwarded through a bypass 162, the cavity formed between the outer tube 131a and the inner tube 135a of the manifold 122, and the exhalant circuit formed between the outer tube 104a and the inner tube 102a of the first coaxial tube type main tube 105a into the forked tube 107. From the forked tube 107, it is either sent to the exhalant gas meter or ventilator (not shown) or discharged directly into the ambient air. An annular groove 166 is provided at one point on the periphery of the inner cylinder of the diaphragm 156. When the diaphragm 156 is pushed up during the period of exhalation, the annular groove 166 is expanded to give rise to a larger gap between the edge of the inner cylinder and the diaphragm than when the diaphragm has a simple flat shape. Thus, the annular groove improves the efficiency of exhalation.

During the flow of the exhalant gas, the pressure of the air applied through the lead tube 158 to the upper pressure chamber 159 in the diaphragm 156 of the exhalation valve 137 is decreased to a great extent. Consequently, the exhalant gas in the inner cylinder 154 pushes the diaphragm 156 upwardly and finds its way into the cavity 163 outside the inner cylinder 154. When the positive-end-epiratory pressure (PEEP) therapy is called for, the pressure of air applied to the interior of the pressure chamber 159 is not wholly released. Instead, it is maintained at a feeble level of 5 cm $H_2O$, for example, least the inner pressure of the patient's lungs should fall to 0 cm $H_2O$ at the end of the exhalation. Of course in the case of a patient who does not require the positive end-expiratory pressure therapy, the pressure chamber can be adjusted so that the pressure of air in this chamber may fall to 0 cm $H_2O$ at the end of the exhalation.

The breathing circuit illustrated in FIGS. 21–27 is operated in much the same way as the circuit illustrated in FIGS. 17–20, with the exception that the inhalant gas lead tube 275 is connected to the respirator or anesthetizer (not shown) and the exhalant gas lead tube 276 is either connected to the exhalant gas meter (not shown) or opened into the ambient air. Also, the exhalant gas meter may be connected to the port 260 in place of the exhalant gas lead tube.

The inventor conducted the following experiments for the purpose of confirming the effect of this invention.

EXPERIMENT 1

As the outer tube 104, a corrugated tube having an average wall thickness, $t_0$ of 0.75 mm, an outside diameter of 23.5 mm at the groove, an outside diameter of 27.5 mm at the ridge, and a length of 1 m was prepared. As the inner tube 102, three corrugated tubes, A–C, having a common outside diameter of 10.5 mm at the groove, a common outside diameter of 13.5 mm at the ridge, a common length of 1 m, and different average wall thicknesses, $t_1$, of 0.45 mm, 0.75 mm, and 1.5 mm. Then by using these outer tubes 104 and inner tubes 102, three tubes, A–C, of the construction illustrated in FIG. 1 were assembled.

Separately, a control tube D was produced with two corrugated tubes each having an outside diameter of 23.5 mm at the groove, an outside diameter of 27.5 mm at the ridge, an average wall thickness of 0.75 mm, and a length of 1 m. One of the corrugated tubes was used as an inhalant circuit and the other as an exhalant circuit, with their leading ends connected to each other through the medium of a Y-shaped tube.

The inhalant inlet of each of the four tubes, A through D, was connected to a combination heater and humidifier and a respirator and the exhalant outlet connected to the respirator. On the other hand, the patient side connector was connected to a model lung. At the prevalent room temperature of 22° C., the operation of the combination heater and humidifier was controlled to produce a constant humidity of 100% and a varying temperature (VCT) as shown in Table 1 to keep the temperature in the model lung in the range of 37.4° to 37.6° C. and the relative humidity at 100%. Then, model test of artificial respiration was performed under the conditions of 50 ml/cm $H_2O$ of compliance, 650 cc of ventilation volume per cycle, 1.5 sec of inhalant period, and 2.5 sec of exhalant period. After this artificial respiration was continued for ten hours, the inhalant gas was tested for average temperature at the patient's mouth (LCT) and for the amount of moisture forming dew in the duct at the end of the ten hours (cc). The results are shown in Table 1.

TABLE 1

| VCT (°C.) | A ($t_1/t_0$ = 60%) | | B ($t_1/t_0$ = 100%) | | C ($t_1/t_0$ = 200%) | | D (outer tube only) | |
|---|---|---|---|---|---|---|---|---|
| | LCT (°C.) | Moisture (cc) | LCT (°C.) | Moisture (cc) | LCT (°C.) | Moisture (cc) | LCT | Moisture (CC) |
| 40 | 36.5 | 49 | 36.7 | 46 | 37.0 | 42 | 31.0 | 11.2 |
| 37 | 35.3 | 21 | 35.3 | 21 | 35.3 | 21 | — | — |
| 36 | 34.9 | 13 | 34.6 | 17 | 34.3 | 20 | — | — |
| 35 | 34.5 | 6 | 33.9 | 13 | 33.6 | 16 | — | — |
| 34 | 33.7 | 3 | 33.1 | 10 | 32.8 | 14 | — | — |
| 33 | 32.8 | 1 | 32.3 | 8 | 32.0 | 11 | — | — |

EXPERIMENT 2

As the outer tube 104, a corrugated tube made of polyethylene and measuring 1 m in length was prepared. In this case, the corrugated tube was so fabricated as to have an wall thickness of 0.75 mm, a difference ($\Phi - \phi$) of 4 mm between the outside diameter at the ridge and that at groove, a radius of curvature (r) of 1 mm at the peak of the ridge, and an outside diameter ($\phi$) of 23.5 mm at the groove. The ratio of elongation of the tube was 12.5% under application of an inner pressure of 50 cm $H_2O$.

Separately, corrugated tubes, E through L, of varying particulars indicated in Table 2 were prepared. All these corrugated tubes shared a wall thickness of 0.75 mm, a length of 1 m, and an outside diameter ($\phi$) of 10.5 mm.

TABLE 2

| Corrugated inner tube | Ratio of elongation under inner pressure of 50 cm $H_2O$ (%) | $\Phi - \phi$ (mm) | $\gamma$ (mm) | Material of tube | Hardness (Shore D) |
|---|---|---|---|---|---|
| E | 8.3 | 3 | 1 | Polyethylene | 55D |
| F | 12.5 | 4 | 1 | Polyethylene | 55D |
| G | 17.6 | 5 | 1 | Polyethylene | 55D |
| H | 8.8 | 4 | 0.7 | Polyethylene | 55D |
| I | 19.0 | 4 | 1.5 | Polyethylene | 55D |
| J | 5.7 | 3 | 0.7 | Polyethylene | 55D |
| K | 7.9 | 4 | 1 | Polyethylene | 80D |
| L | 22.2 | 4 | 1 | EVA* | 35D |

*Ethylene-vinyl acetate copolymer

A total of eight tubes, I through VIII, constructed as illustrated in FIG. 1 were produced by using the corrugated tubes, E through L, as their respective inner tubes 102.

Separately, a tube, IX, was produced by using two corrugated tubes, one as an inhalant circuit and the other as an exhalant circuit, with their leading ends connected to a Y-shaped tube. Besides, by following the disclosure of Japanese Published Unexamined Patent No. 150893/1979 and using the corrugated tubes, E and F, tubes X, XI were constructed as illustrated in FIG. 1, except that no inner tube fixing mouth was used in the connector and the inner tube was fixed inside the connector through the medium of spacers.

The total of 11 circuits were tested for elongation under application of pressures 30 cm H₂O and 60 cm H₂O to the inhalant circuits (inner tubes or inhalant tubes). The results are shown in Table 3.

TABLE 3

| Duct | Inner tube | Elongation (%) 30 cm H₂O | Elongation (%) 60 cm H₂O |
|---|---|---|---|
| I | E | 2.5 | 5 |
| II | F | 4.5 | 9 |
| III | G | 5.2 | 10.5 |
| IV | H | 2.6 | 5.2 |
| V | I | 5.4 | 10.8 |
| VI | J | 1.6 | 3.3 |
| VII | K | 2.4 | 4.8 |
| VIII | L | 5.7 | 11.5 |
| IX | Outer tube alone | 7.5 | 15 |
| X | E | 7.5 | 15 |
| XI | F | 7.5 | 15 |

The effect of this invention is evident from the results given above. In the circuits, X and XI, the spacers came off the inner tubes during the test.

When various ducts were produced exactly as described above in the construction of FIGS. 17-20, they yielded results equivalent to the results shown in Table 3.

EXPERIMENT 3

Conventional corrugated tubes not provided with means for restricting expansion and contraction of tubes and illustrated corrugated tubes of the present invention provided with means for restricting the expansion and contraction of tubes were tested for elongation (in terms of increase in volume) under application of an internal pressure of 30 cm H₂O, to obtain the results shown in Table 4. The sample tubes used for the test were as shown below. The volumes increased owing to the elongation of corrugated tubes as found in the test are shown in Table 4 given below. The dimensions of the sample tubes were identical unless otherwise specified. (Dimensions of sample tube)

(1) Conventional corrugated circuit (provided with no means for restricting expansion and contraction): Average wall thickness (at groove) 0.5 mm, (at ridge) 0.3 mm, pitch of corrugation 3.5 mm, outside diameter at ridge 26 mm, outside diameter at groove 22 mm, length 1000 mm, and volume 500 cc.
(2) Circuit XII, of this invention, constructed as illustrated in FIGS. 8–9: Width of smooth-faced strip 2 mm
(3) Circuit, XIII, of this invention, constructed as illustrated in FIGS. 10–11: Length of smooth-faced strip 20 mm, width of smooth-faced strip 2 mm
(4) Circuit, XIV, of this invention, constructed as illustrated in FIG. 12: Pitch of smooth-faced strips 80 mm, width of smooth-faced strip 2 mm
(5) Circuit, XV, of this invention, constructed as illustrated in FIG. 13: Pitch of smooth-faced strips 40 mm, width of smooth-faced strip 2 mm
(6) Circuit, XVI, of this invention, constructed as illustrated in FIG. 15: Length of smooth-faced cylindrical portion 10.5 mm, number of ridges in smooth-faced portion n=3, pitch p=4.5

TABLE 4

| Sample Circuit | Increase in volume (cc) | Ratio of increase in volume (%) | Proportion of increase in Volume of circuit of this invention to increase in volume of conventional circuit (%) |
|---|---|---|---|
| Conventional circuit | 37.5 | 7.5 | — |
| Circuit XII | 15.6 | 3.1 | 42 |
| Circuit XIII | 20.3 | 4.1 | 54 |
| Circuit XIV | 23.4 | 4.7 | 62 |
| Circuit XV | 18.1 | 3.6 | 48 |
| Circuit XVI | 23.4 | 4.7 | 62 |

It is noted from the test results given above that for the fixed inner pressure of 30 cm H₂O, the increases in volume of the corrugated tubes of the present invention provided with means for restricting expansion and contraction of the tube are about 40 to 60% of the increases in volume of the conventional corrugated tubes. The dead spaces in the tubes were small. These results indicate that when these corrugated tubes are used for a respiratory system, oxygen or other inhalant gas can be fed to the patient at a feed volume fixed at first. Further, the means used in this invention for restricting expansion and contraction of the tube is capable of lessening the elongation and also decreasing the contraction of the corrugated tube. It, therefore, precludes the possibility that oxygen or other inhalant gas will be fed in a volume larger than was first fixed. When a corrugated tube fitted with the means of this invention for restricting expansion and contraction of the tube was wound tightly around the periphery of a circular column 50 mm in diameter without application of tension to the tube, the cavity of the tube remained uncollapsed similarly to the conventional corrugated tube. From the results indicated above, it is easily noted that the corrugated tube provided with means for restricting expansion and contraction of the tube according to this invention notably improves the reliability of the respiratory system such as, for example, the respiratory duct. The present invention, therefore, enjoys great practical utility.

In accordance with the present invention, corrugated tubes having a continuous or discontinuous spiral ridge, when provided with means for restricting expansion and contraction of the tube, are capable of lessening the increase in volume by 58% in the construction of FIG. 8, 46% in the construction of FIG. 10, 38% in the construction of FIG. 12, 52% in the construction of FIG. 13, and 38% in the construction of FIG. 15 respectively as compared with the conventional tubes. The increase of dead space due to the elongation of corrugated tubes are proportionally lessened. With such corrugated tubes of this invention, therefore, the air, oxygen or other inhalant gas can be supplied at a feed volume approximating the level initially fixed. Because a tube which shows no heavy elongation shows no heavy contraction either, the corrugated tube of this invention has no possibility of suffering the amount of oxygen, etc. fed to the patient to be increased beyond the fixed level owing to a contraction of the tube.

In the case of the corrugated tube incorporating smooth-faced cylindrical portions, the expansion and contraction of the corrugated tube are notably lessened by constructing the tube so that the tube satisfies the conditions, $l \geqq 30$ mm and $p<l<np$, wherein l stands for the length of the smooth-faced cylindrical portion and n for the number of ridges in the corrugated portion ($n \geqq 2$). With this corrugated tube, therefore, supply of the inhalant gas is stabilized.

EXPERIMENT 4

Circuits were constructed as illustrated in FIGS. 21-27. One end of each of the circuits was connected through a combination heater and humidifier to a respirator and the other end was connected to a model lung maintained at a temperature of 37° C. and a relative humidity of 100%. The circuits were tested for their properties. The results are shown in Table 5.

In this case, in the breathing circuit, XVII, of this invention illustrated in FIGS. 21-27, a corrugated tube of polyethylene having an inside diameter 13.5 mm at the groove, an inside diameter 15 mm at the ridge, an average wall thickness of 0.3 mm, and a length of 60 cm was used as the inner tube 202 forming part of the coaxial tube 205 and a corrugated tube of polyethylene having an inside diameter 23.5 mm at the groove, an inside diameter of 28 mm at the ridge, an average wall thickness of 1 mm, and the same length of 60 cm as the inner tube 102 was used as the outer tube 204 forming part of the coaxial tube 205. Two corrugated tubes of polyethylene each having an inside diameter of 23.5 mm at the groove, an inside diameter of 28 mm at the ridge, an average wall thickness of 1 mm, and a length of 60 cm were used respectively as the exhalant tube 276 and the inhalant tube 275 each of one-wall construction.

Separately, four corrugated tubes of polyethylene each having an inside diameter of 23.5 mm at the groove, an inside diameter of 28 mm at the ridge, an average wall thickness of 1 mm, and a length of 60 cm were used. These two corrugated tubes were connected at one end to a Y-shaped tube and at the other end of the two tubes respectively to a nebulizer and an exhalation valve, and at the other end of the rest of two tubes to a combination heater and humidifier via a respirator, to complete a breathing circuit XVIII. A coaxial tube consisting of a corrugated outer tube of polyethylene having an inside diameter of 23.5 mm at the groove, an inside diameter of 28 mm at the ridge, an average wall thickness of 1 mm, and a length of 120 cm and an inner tube of polyvinyl chloride having an inside diameter of 11 mm, an average wall thickness of 1.5 mm, and a length of 120 cm was connected at one end to a connector and connected at the other end via a respirator to a combination heater and humidifier, to complete a breathing circuit XIX. Besides, by using the same coaxial tube as the circuit XVII, a circuit XX of a construction of FIGS. 17-20 was produced.

TABLE 5

| Circuit | Temperature of combination heater and humidifier (°C.) | Temperature of inhalant gas at mouth of model lung (°C.) | Moisture deposited in circuit Humidifier to connector (g/m²) | Moisture deposited in circuit Connector to model lung (g/m²) | Resistance (cm H₂)/l/sec Inhalant gas | Resistance (cm H₂)/l/sec Exhalant gas |
|---|---|---|---|---|---|---|
| XVII | 32.5–34.5 | 32.5–33.3 | 5.0 | 0.3 | 1.8 | 2.1 |
| XVIII | 38–40 | 32.6–33.2 | 15.5 | 5.0 | 0.7 | 1.5 |
| XIX | 33.5–35.5 | 32.3–33.4 | 6.5 | | 3.0 | 2.1 |
| XX | 32.3–34.3 | 33.2–33.4 | 4.7 | 0.3 | 7.4 | 2.2 |

As described above, the breathing circuit of the present invention comprises a coaxial tube type main tube comprising a flexible inner tube constituting an inhalant circuit and a corrugated outer tube having a larger average wall thickness than the aforementioned inner tube, encircling the periphery of the inner tube, and defining an exhalant circuit in conjunction with the inner tube; and an inner tube retaining member disposed at least at one end of the aforementioned coaxial tube type main circuit and serving to keep the inner tube and the outer tube at a fixed distance from each other. In this breathing circuit, the heat loss which occurs when the inhalant gas heated in advance to a temperature below the temperature of the lungs is fed through the circuit is notably lessened as compared with a breathing circuit which does not use the construction mentioned above. The heat loss is lessened to a greater extent when the average wall thickness of the inner tube is 20 to 90% of the average wall thickness of the outer tube and the average wall thickness of the inner tube falls in the range of 0.2 to 1 mm.

The temperature drop of the inhalant gas is small even when the length of the coaxial tube is very large. When the inhalant gas heated to a temperature below the temperature of the lungs is forwarded by this breathing circuit, it can be delivered to the mouth of the patient at an optimum temperature of 32° to 35° C. Even when the artificial respiration is carried out over a very long period, the amount of moisture for forming dew is small because the temperature drop is small. Further, the range of heating temperature of the inhalant gas allowed for the purpose of enabling the inhalant gas to be delivered to the patient's mouth at the optimum temperature of 32° to 35° C. is widened because of the small temperature drop. This delivery of the inhalant gas to the patient's mouth at the optimum temperature can be continued stably even when a variation of temperature or some other unexpected trouble occurs on the combination heater and humidifier.

In addition to the outstanding effect mentioned above, the breathing circuit of this invention enjoys an advantage that the possibility of the circuit being collapsed by the phenomenon of kinking is very remote because the outer tube has a corrugated wall. Since the breathing circuit of this invention is so constructed that the terminal portions of the outer and inner tubes at the patient side end of the coaxial tube are both fixed to each other through the medium of the inner tube, the possible elongation of the circuit due to an increase in the internal pressure is lessened and the mechanical dead space is likewise decreased. Consequently, the set value of ventilation volume of the respirator and the actual value of ventilation volume have a small difference. When the nebulizer is disposed within the connector, the inhalant gas can be loaded with the aerosol of such a medicinal solution as bronchodilater or sputum dissolver. The nebulizer can be used conveniently in this manner. Since the nebulizer can be positioned in the breathing circuit more closely to the patient's mouth, the efficiency of the inhalation of aerosol is heightened.

Moreover, when an exhalation valve is provided within this bypass, then the circuit can be used effectively with a respirator which is devoid of an exhalation valve. The circuit, consequently, enjoys enhanced usefulness. Application of a stated positive pressure (such as 5 cm $H_2O$) to the exhalation valve during the period of exhalation lessens the possible collapse of alveolus of the lungs, making possible the administration of the PEEP therapy.

In this case, this effect is further enhanced when the division of the ratio of elongation of the inner tube by that of the outer tube gives a quotient of not more than 0.8.

Required reduction in the ratio of elongation of the inner tube can be accomplished by making the difference between the outside diameter at the ridge and that at the groove in the inner tube smaller than the difference in the outer tube (so that the ratio of the two differences will fall in the range of 0.20 to 0.95). When this requirement is satisfied, the aforementioned effect of this invention is advantageously manifested. The reduction mentioned above can otherwise be materialized by making the radius of curvature at the peak of the ridges of corrugation of the inner tube smaller than that of the outer tube (preferably the ratio between the two radii falling in the range of 0.15 to 0.95). The same effect is also obtained by producing the inner tube with a material of greater rigidity than the material of the outer tube.

When the coaxial tube construction is limited to the portion of the duct intervening between the manifold and the patient, there is ensured an effect that the resistance offered by the inhalant gas and that offered by the exhalant gas are lessened.

As is clear from the foregoing experiments, in the circuit having a coaxial construction only between the manifold and the patient, the heat loss is equally lessened and the resistance of the inhalant gas and that of the exhalant gas are notably lowered as compared with the circuit having a coaxial construction throughout the entire length between the respirator and the patient. For fixed resistances of the inhalant gas and the exhalant gas, the tube diameter is decisively smaller in the duct having the coaxial construction in the limited portion than in the circuit having the coaxial construction throughout its entire length. The circuit of interest, therefore, has an effect of simplifying the coaxial tube.

What is claimed is:

1. A breathing circuit which comprises:
   coupling means adapted to be coupled to a patient and through which the patient can inhale and exhale;
   a source of supply fluid for the patient;
   a coaxial tube type main tube coupled between said coupling means and said supply source, and comprising an inner flexible tube constituting an inhalant circuit and a corrugated outer tube having a larger average wall thickness than said inner tube, said outer tube encircling the periphery of said inner tube and defining an exhalant circuit in conjunction with said inner tube; and
   an inner tube retaining member disposed at least at one end of said coaxial tube type main tube for keeping said inner tube and said outer tube at a prescribed distance from each other;
   the average wall thickness of said inner tube being 20 to 60% of the average wall thickness of said outer tube.

2. A breathing circuit according to claim 1, wherein the flexible inner tube of the coaxial tube type main tube is a corrugated tube.

3. A breathing circuit according to claim 2, wherein the division of the ratio of elongation of the inner tube by that of the outer tube gives a quotient of not more than 0.8.

4. A breathing circuit according to claim 2, wherein said corrugated outer tube and said corrugated flexible inner tube have alternate ridges and grooves; and the difference between the outside diameter at the ridges and that at the grooves in the corrugated inner tube is smaller than the difference between the outside diameter at the ridges and that at the grooves in the corrugated outer tube.

5. A breathing circuit according to claim 4, wherein the difference between the outside diameter at the ridges and that at the grooves in the inner tube, when divided by the difference between the outside diameter at the ridges and that at the grooves in the outer tube, gives a quotient falling in the range of 0.20 to 0.95.

6. A breathing circuit according to claim 4, wherein the difference between the outside diameter at the ridges and that at the grooves in the inner tube, when divided by the difference between the outside diameter at the ridges and that at the grooves in the outer tube, gives a quotient falling in the range of 0.4 to 0.8.

7. A breathing circuit according to claim 1, wherein the flexible inner tube of the coaxial tube type main tube is a smooth-faced tube.

8. A breathing circuit according to claim 1, wherein said supply source includes a combination gas inlet andd outlet; and
   the inner tube retaining member is coupled to said inner and outer tubes, and comprises:
   an outer tube member communicating with said combination gas inlet and outlet, and an inner tube member formed coaxially with said outer tube member;
   at least two openings are formed between said outer tube and said inner tube; and
   means connecting said outer tube and said inner tube to each other at portions thereof between said openings.

9. A breathing circuit according to claim 8, wherein the inner tube retaining member comprises an outer tube member and an inner tube member disposed so that said inner tube member protrudes relative to said outer tube member near one end of said outer tube member.

10. A breathing circuit according to claim 8, wherein said openings are spaced by substantially equal distances.

11. A breathing circuit according to claim 10, wherein the portions between said openings are in the shape of columns.

12. A breathing circuit according to claim 1, wherein the average wall thickness of the inner tube falls in the range of 0.2 to 1 mm.

13. A breathing circuit according to claim 1, wherein the average wall thickness of the outer tube falls in the range of 0.4 to 1.5 mm.

14. A breathing circuit according to claim 1, wherein the material forming the inner tube has a higher rigidity than the material forming the outer tube.

15. A breathing circuit according to claim 1, wherein the corrugated outer tube is provided with means for restricting expansion and contraction of the outer tube in the axial direction.

16. A breathing circuit according to claim 15, wherein the means for restricting expansion and contraction of the outer tube comprises at least one flat, smooth-faced strip extended in the axial direction of the outer tube, raised in the radial direction to a level falling between the ridges and the grooves of the corrugated outer tube portion, and merged into the ridges of corrugation.

17. A breathing circuit according to claim 15, wherein the means for restricting expansion and contraction of the outer tube comprises at least one smooth-faced strip spiralled around the periphery of the outer tube, raised in the radial direction to a level falling between the ridges and the grooves of the corrugated outer tube portion, and merged into the ridges of corrugation.

18. A breathing circuit according to claim 15, wherein the means for restricting expansion and contraction of the outer tube comprises smooth-faced cylindrical portions disposed alternately with the corrugated portions.

19. A breathing circuit according to claim 18, wherein the length, l, in the axial direction of the smooth-faced cylindrical portions is not more than 30 mm and the smooth-faced cylindrical portions and the corrugated portions satisfy the condition, $p<l<np$, wherein n stands for the number of ridges in the corrugated portions and p for the pitch in mm.

20. A breathing circuit according to claim 18, wherein the radius of the smooth-faced cylindrical portions is not more than that of the ridges in the corrugated portions.

21. A breathing circuit according to claim 18, wherein the means for restricting expansion and contraction of the outer tube comprises smooth-faced cylindrical portions and at least one of (i) at least one smooth-faced strip extended in the axial direction through the corrugated portions and (ii) at least one smooth-faced strip spiralled around the corrugated portion and raised in the radial direction to a level falling between the ridges and the grooves of the corrugated portions.

22. A breathing circuit according to claim 1, wherein said supply source includes a coaxial tube manifold; and the coaxial tube type main tube comprises a coaxial tube connected through the medium of said coaxial tube manifold.

23. A breathing circuit according to claim 22, wherein the manifold has a nebulizer disposed in the path of the inner tube.

24. A breathing circuit according to claim 22, wherein the manifold has an exhalant circuit including a bypass coupled around the nebulizer, said bypass including therein an exhalation valve.

25. A breathing circuit which comprises:
a coaxial tube type main tube comprising an inner flexible tube constituting an inhalant circuit and a corrugated outer tube having a larger average wall thickness than said inner tube, said average wall thickness of said inner tube being 20 to 60% of the average wall thickness of said inner tube, said outer tube encircling the periphery of said inner tube and defining an exhalant circuit in conjunction with said inner tube;
an inner tube retaining member disposed at one end of said coaxial tube type main tube and maintaining said inner tube and said outer tube at a prescribed distance from each other;
a manifold disposed at the other end of said coaxial tube type main tube and provided with an exhalation valve and a nebulizer;
said manifold comprising:
an inner tube portion communicating with said nebulizer and connected to said flexible inner tube,
an outer tube portion disposed on the periphery of said inner tube portion, means being provided to close said outer tube portion relative to said nebulizer, and said outer tube portion being connected to said corrugated outer tube,
an exhalation valve communicating with said outer tube portion,
and an inhalant gas inlet tube portion communicating with said nebulizer so that said inhalant gas inlet portion and said inner and outer tube portions are all in communication, and that an exhalation flow path is provided to said exhalation valve; and
an inhalant gas lead tube connected to said inhalant gas inlet tube portion.

26. A breathing circuit according to claim 25 further comprising an exhalant gas lead tube connected to said exhalation valve.

* * * * *

UNITED STATES PATENT AND TRADEMARK OFFICE
CERTIFICATE OF CORRECTION

PATENT NO. : 4,463,755

DATED : August 7, 1984

INVENTOR(S) : Tatsuo SUZUKI

It is certified that error appears in the above-identified patent and that said Letters Patent is hereby corrected as shown below:

COLUMN 22 (Claim 8), line 39, after "gas inlet" change "andd" to --and--;

COLUMN 24 (Claim 25), line 17, after "thickness of said" change "inner" to --outer--.

Signed and Sealed this

Fifth Day of March 1985

[SEAL]

Attest:

DONALD J. QUIGG

Attesting Officer

Acting Commissioner of Patents and Trademarks